United States Patent
Dishisha et al.

(10) Patent No.: US 10,053,411 B2
(45) Date of Patent: Aug. 21, 2018

(54) 3-HYDROXYPROPIONALDEHYDE DETECTION AND EXTRACTION

(71) Applicant: EVONIK DEGUSSA GMBH, Essen (DE)

(72) Inventors: Tarek Dishisha, Beni-Suef (EG); Rajni Hatti Kaul, Lund (SE); Roya R. R. Sardari, Lund (SE); Bastian Grund, Recklinghausen (DE); Oliver Thum, Ratingen (DE)

(73) Assignee: EVONIK DEGUSSA GMBH, Essen (DE)

( * ) Notice: Subject to any disclaimer, the term of this patent is extended or adjusted under 35 U.S.C. 154(b) by 0 days.

(21) Appl. No.: 15/827,173

(22) Filed: Nov. 30, 2017

(65) Prior Publication Data
US 2018/0170851 A1 Jun. 21, 2018

(30) Foreign Application Priority Data
Dec. 20, 2016 (EP) .................................... 16205214

(51) Int. Cl.
*C07C 45/79* (2006.01)
(52) U.S. Cl.
CPC .................................... *C07C 45/79* (2013.01)

(58) Field of Classification Search
CPC ...................................................... C07C 45/79
See application file for complete search history.

(56) References Cited

U.S. PATENT DOCUMENTS

2012/0034665 A1   2/2012  Haas et al.

FOREIGN PATENT DOCUMENTS

WO    2010/127970 A2   11/2010

*Primary Examiner* — Sikarl A Witherspoon
(74) *Attorney, Agent, or Firm* — Smith, Gambrell & Russell, LLP

(57) ABSTRACT

The present invention relates to a method of extracting 3-hydroxypropionaldehyde (3-HPA) and/or derivatives thereof from an aqueous solution comprising 3-HPA, the method comprising:
(a) contacting the aqueous solution with chitosan and/or chitosan comprising polymers;
(b) separating the 3-HPA bound chitosan and/or chitosan comprising polymers; and
(c) washing the 3-HPA bound chitosan and/or chitosan comprising polymers at least once with a washing medium;
wherein 3-HPA and/or derivatives thereof is in the washing medium.

15 Claims, 2 Drawing Sheets

US 10,053,411 B2

3-HYDROXYPROPIONALDEHYDE DETECTION AND EXTRACTION

FIELD OF THE INVENTION

The present invention relates to a method of identifying and/or extracting 3-hydroxypropionaldehyde (3-HPA) and/or derivatives thereof from an aqueous solution. In particular, the method involves contacting the 3-HPA with at least one 3-HPA scavenging agent such as chitosan and/or chitosan polymers.

BACKGROUND OF THE INVENTION 3-hydroxypropionaldehyde (3-HPA) is a useful raw material for the production of several compounds such as acrolein, acrylic add and/or 1,3-propanediol. The production and extraction of 3-HPA is thus important for the production of these final products. Currently, 3-HPA is produced from renewable raw materials using microbial means. One of the most commonly used methods includes the production of 3-HPA from glycerol using bacterial cells. However, 3-HPA in low concentrations is toxic to the cells and results in the cells dying and/or producing 3-HPA at low efficiency. The cells can thus not be used for a long period of time and 3-HPA production stops.

One way to protect the cells from being killed and to maintain the production of 3-HPA at high yield is to extract the 3-HPA from the production medium as it is produced or before it reaches toxic levels. This allows the cells to be reused and also allows for the unreacted carbon source to be used for production. There are several methods known in the past for 3-HPA removal. This includes in-situ reversible binding processes, use of in-situ semicarbazide-functionalized resins, chromatographic purification and the like. However, these methods are known to be inefficient and costly. These disadvantages do not allow for economic production and extraction of 3-HPA on a larger scale.

WO 2010/127970 discloses another method of in-situ removal of 3-HPA directly from the production medium. However, this method involves a complicated separation of 3-HPA that uses adsorbents such as hydrazides, hydrazines, hydrogen sulfites, sulfites, metabisulfites or pyrosulfites and the like. This makes the separation method again very costly.

Accordingly, there is a need in the art for an efficient and cost-effective selective purification process for 3-HPA where the cells may be reused for a longer period of time.

DESCRIPTION OF THE INVENTION

The present invention attempts to solve the problems above by providing a means of separating 3-hydroxypropionaldehyde (3-HPA) from an aqueous solution using non-toxic means. These non-toxic means may involve the use of chitosan and/or chitosan comprising polymers that may have a strong binding affinity towards 3-HPA. 3-HPA bound chitosan and/or chitosan polymers may then be separated using basic methods known in the art and the 3-HPA may be separated from the chitosan and/or chitosan comprising polymers by a washing step using a washing medium. The use of chitosan and/or chitosan comprising polymers in the method of extracting 3-HPA from an aqueous medium allows the process of extraction to be non-toxic to any other cell, microorganism etc. that is in the aqueous medium.

According to one aspect of the present invention, there is provided a method of extracting 3-hydroxypropionaldehyde (3-HPA) and/or derivatives thereof from an aqueous solution comprising 3-HPA, the method comprising:
(a) contacting the aqueous solution with chitosan and/or chitosan comprising polymers;
(b) separating the 3-HPA bound chitosan and/or chitosan comprising polymers; and
(c) washing the 3-HPA bound chitosan and/or chitosan comprising polymers with at least one washing medium;
wherein 3-HPA and/or derivatives thereof is in the washing medium.

In particular, the washing medium may be selected from the group consisting of water, an acid and mixtures thereof.

3-HPA and/or derivatives thereof are known to include aldehydes in an aqueous solution that can occur in different forms such as for example monomeric, dimeric and/or hydrated forms (Vollenweider, S (2003), *J. Agric. Food Chem.* 51 (11): 3287-93). For example, in an aqueous solution, 3-HPA may undergo a revisable dimerization and hydration that may result in an equilibrium of 3-hydroxypropionaldehyde, 1,1,3-trihydroxypropane, and 2-(2-hydroxyethyl)-4-hydroxy-1,3-dioxane. A skilled person thus understands 3-HPA and/or derivatives thereof in an aqueous solution to include the above mentioned forms of 3-HPA among others. Chitosan is a linear polymer of glucosamine units. The presence of a primary amine group allows it to be structurally distinguished from cellulose. The presence of amine groups in chitosan confers interesting and potentially useful chemical and physical properties on the polymer. Although chitosan is not water soluble under neutral or alkaline conditions, under mildly acidic conditions (pH less than about 6) the amine groups are protonated and the polycationic polymer becomes water soluble. At neutral and alkaline pH, the amine groups are deprotonated and the neutral chitosan polymer is water-insoluble. A skilled person would understand that the chitosan may remain water-insoluble in the method according to any aspect of the present invention when the 3-HPA bound chitosan and/or chitosan comprising polymers is washed in step (c) with the washing medium. The water-insolubility of the chitosan in the 3-HPA bound chitosan and/or chitosan comprising polymers allows for essentially all the 3-HPA to be eluted in the washing medium and the chitosan and/or chitosan comprising polymers to remain in their undissolved form. This undissolved form may be in a solid or gel like form. In one example, when the washing medium used may be an acid, the consistency of the chitosan and/or chitosan comprising polymers during and/or after step (c) may depend on the concentration of the acid and the time of contact between the acid and the chitosan. It would be within the routine techniques of a skilled person to vary these factors to ensure the maximum yield of 3-HPA is extracted according to aspect of the present invention. In one example, the pH of the aqueous medium may be about 7 when the binding capacity of chitosan to 3-HPA is highest.

The term 'chitosan and/or chitosan comprising polymers' as used herein includes any chitosan known in the art. Such a chitosan may be isolated from natural sources, or may be commercially-available chitosan, such as from any suppliers (e.g., Aldrich, Sigma), without regard to the particular average molecular weight of the polymer. For example, chitosan and/or chitosan comprising polymers used according to any aspect of the present invention may include "low" (typically above about 10,000 g/mol), "medium" (typically about 100,000 to 300,000 g/mol), or "high" (typically above about 300,000 g/mol) molecular weight chitosan polymers. As is well known in the art, chitosan may be conventionally produced by deacetylation of chitin. Chitosan used according to any aspect of the present invention may be of various grades, having different average molecular weight and may have undergone different extents of deacetylation. Thus, the term "chitosan polymer or oligomer" includes chitosan with complete or nearly complete deacetylation (e.g., 90-100%), or equally chitosan with less complete deacetylation. The term "chitosan comprising polymers" also includes various derivatives of chitosan having the necessary solubility in the reaction solution and having at least a portion of the amino functional group available for reaction. The term 'chitosan and/or chitosan comprising polymers' thus includes naturally occurring chitosan as well as those modified to include new characteristics. Some examples of chitosan comprising polymers include chitosan grafted natural or synthetic polymers that could include copolymers of chitosan with other polymers, or polymers with inherent or covalently bound glucosamine or N-acetyl glucosamine residues. Examples of chitosan comprising polymers may not be limited to O- and N-carboxymethylchitosans, chitosan 6-O-sulfate, N-methylene phosphonic chitosans, trimethylchitosan ammonium, carbohydrate-branched chitosans, chitosan-grafted copolymers and alkylated chitosans. A skilled person would easily be able to identify the chitosan and/or chitosan comprising polymers that would work in any aspect of the present invention. In one example, medium molecular weight chitosan polymers may be used according to any method of the present invention. In particular, the medium molecular weight chitosan polymer has a viscosity of 200-800 cP (1 wt. % in 1% acetic acid—75 to 85% deacetylation). The chitosan polymers may be dissolved in acetic acid before being used in the method according to any aspect of the present invention. In particular, the acetic acid may have a concentration of 2 wt %, 4 wt % or 6 wt %. Even more in particular, the acetic acid may have a concentration of 2 wt %. In one example, the medium molecular weight chitosan polymers may be dissolved in 2 wt % acetic acid before being used in the method according to any aspect of the present invention.

The term "contacting", as used herein, means bringing about direct contact between the aqueous medium comprising 3-HPA and the chitosan and/or chitosan comprising polymers according to any aspect of the present invention in step (a). For example, the chitosan and/or chitosan comprising polymers may be added to the aqueous medium comprising 3-HPA. In another example, the aqueous medium comprising the 3-HPA may be added into a vessel comprising chitosan and/or chitosan comprising polymers. In any case, the 3-HPA comprising aqueous medium is brought into contact with chitosan and/or chitosan comprising polymers.

The term "an aqueous solution" or "medium" comprises any solution comprising water, mainly water as solvent that may be used to dissolve 3-HPA. In one example where 3-HPA may be formed by biotechnological means, the aqueous medium may also comprise at least one microbial cell type. The aqueous medium may then be used to keep the cells at least temporarily, in a metabolically active and/or viable state and comprises, if such is necessary, any additional substrates besides water. The person skilled in the art is familiar with the preparation of numerous aqueous solutions, usually referred to as media that may be used to keep cells, for example LB medium in the case of *Escherichia coli*, ATCC1754-Medium may be used in the case of *Clostridium ljungdahlii*. It is advantageous to use as an aqueous solution a minimal medium, i.e. a medium of reasonably simple composition that comprises only the minimal set of salts and nutrients indispensable for keeping the cells in a metabolically active and/or viable state, by contrast to complex media, to avoid dispensable contamination of the products with unwanted side products. For example, M9 medium may be used as a minimal medium. The cells are incubated with the carbon source sufficiently long enough to produce the desired product, 3-HPA and variants thereof. For example for at least 1, 2, 4, 5, 10 or 20 hours. The temperature chosen must be such that the cells remain catalytically competent and/or metabolically active, for example 10 to 42° C., preferably 30 to 40° C., in particular, 32 to 38° C. in case the cell is a *C. ljungdahlii* cell. In one example, the aqueous medium and conditions are maintained for 3-HPA production by at least one bacterial cell. The bacterial cell may be selected from the group consisting of a strain from the *Citrobacter* sp., *Clostridium* sp., *Enterobacter* sp., *Klebsiella* sp., and *Lactobacillus* sp. which naturally produce 3-HPA. In particular, the bacterial cell may be selected from the group consisting of *Citrobacter. freundii*, *C. butyricum*, *C. acetobutylicum*, *E. agglomerans*, *L. reuteri*, *K. pneumoniae* and the like. In one example, the bacterial cell for producing 3-HPA may be at least one recombinant cell that comprises increased expression relative to the wild-type cell of at least one glycerol dehydratase (EC 4.2.1.30).

The recombinant cell used for the production of 3-HPA can be selected from the group consisting of *Abiotrophia, Acaryochloris, Accumulibacter, Acetivibrio, Acetobacter, Acetohaloblum, Acetonema, Achromobacter, Acidaminococcus, Acidimicroblum, Acidiphillum, Acidithiobacillus, Acidobacterium, Acidothermus, Acidovorax, Acinetobacter, Actinobacillus, Actinomyces, Actinosynnema, Aerococcus, Aeromicrobium, Aeromonas, Afipla, Aggregatibacter, Agrobacterium, Ahrensia, Akkermansla, Alcanivorax, Alicycliphilus, Alicyclobacllus, Aliivibrio, Alkalilimnicola, Alkaliphilus, Allochromatium, Alteromonadales, Alteromonas, Aminobacterlum, Aminomonas, Ammonifex, Amycolatopsis, Amycolicicoccus, Anabaena, Anaerobaculum, Anaerococcus, Anaerofustis, Anaerolinea, Anaeromyxobacter, Anaerostipes, Anaerotruncus, Anaplasma, Anoxybacillus, Aqulfex, Arcanobacterlum, Arcobacter, Aromatoleum, Arthrobacter, Arthrospira, Asticcacaulis, Atopobium, Aurantimonas, Azoarcus, Azorhizobium, Azospirillum, Azotobacter, Bacillus, Bartonella, Basfia, Baumannia, Bdellovibrio, Beggiatoa, Beijerinckla, Bermanella, Beutenbergia, Bilidobacterium, Blophila, Blastopirellula, Blautia, Blochmannia, Bordetella, Borrella, Brachybacterlum, Brachyspira, Bradyrhizobium, Brevibacillus, Brevibacterium, Brevundimonas, Brucella, Buchnera, Bulleidia, Burkholdeia, Butyrivibrio, Caldalkalibacillus, Caldanaerobacter, Caldicellulosiruptor, Calditerrivibrio, Caminibacter, Campylobacter, Carboxydibrachlum, Carboxydothermus, Cardiobacterium, Camobacterium, Carsonella, Catenibacterium, Catenulispora, Catonella, Caulobacter, Cellulomonas, Cellvibrio, Centipeda, Chelativorans, Chloroflexus, Chromobacterium, Chromohalobacter, Chthoniobacter, Citrelcella, Citrobacter, Citromicrobium, Clavibacter, Cloacamonas, Clostridlum, Collinsella, Colwellla, Comamonas, Conexibacter, Congregibacter, Coprobacillus, Coprococcus, Coprothermobacter, Coraliomargarita, Coriobacterlum, corrodens, Corynebacterium, Coxiella, Crocosphaera, Cronobacter, Cryptobacterium, Cuprlavidus, Cyanobium, Cyanothece, Cylindrospermopsis, Dechloromonas. Defenibacter, Dehalococcoides, Dehalogenimonas, Deinococcus, Deiftia, Denitrovibrio, Dermacoccus, Desmospora, Desulfarculus, Desulphateibacillum, Desulfitobacterium, Desulfobacca, Desulfobacterium, Desulfobulbus, Desulfococcus, Desulfohalobium, Desulfomicrobium, Desulfonatronospira, Desulforu dis, Desulfotalea, Desulfo-* tomaculum, Desulfovibrio, Desulfurlspirillum, Desulfurobacterlum, Desulfuromonas, Dethiobacter, Dethiosulfovibrio, Dialister, Dichelobacter, Dickeya, Dictyoglomus, Dietzia, Dinoroseobacter, Dorea, Edwardsiella, Ehrlichia, Eikenella, Elusimicrobium, Endoriftia, Enhydrobacter, Enterobacter, Enterococcus, Epulopiscium, Erwinia, Erysipelothrix, Erythrobacter, Escherichia, Ethanoligenens, Eubacterium, Eubacterium, Exiguobacterium. Faecalibacterium, Ferrimonas, Fervidobacterium, Fibrobacter, Finegoldia, Flexistipes, Francisella, Frankia, Fructobacillus, Fulvimarina, Fusobacterium, Gallibacterium, Gallionella, Gardnerella, Gemella, Gemmate, Gemmatimonas, Geobacillus, Geobacter, Geodermatophilus, Glaciecola, Gloeobacter, Glossina, Gluconacetobacter, Gordonia, Granulibacter, Granulicatella, Grimontla, Haemophilus, Hahella, Halanaerobiumns, Haliangium, Halomonas, Halorhodospira, Halothermothrix, Halothiobacillus, Hamiltonella, Helicobacter, Heliobacterium, Herbaspirillum, Herminiimonas, Herpetosiphon, Hippea, Hirschia, Hlstophilus, Hodgkinia, Hoelea, Holdemania, Hydrogenivirga, Hydrogenobaculum, Hylemonella, Hyphomicrobium, Hyphomonas, Idiomarina, Ilyobacter, Intrasporangium, Isoptericola, Isosphaera, Janibacter, Janthinobacterium, Jonesia, Jonquetella, Kangiella, Ketogulonicigenium, Kineococcus, Kingella, Klebslella, Kocuria, Koribacter, Kosmotoga, Kribbella, Ktedonobacter, Kytococcus, Labrenzia, Lactobacius, Lactococcus, Laribacter, Lautropia, Lawsonia, Legionella, Leifsonia, Lentisphaera, Leptolyngbya, Leptospira, Leptothrix, Leptotrichia, Leuconostoc, Liberibacter, Limnobacter, Listeria, Loktanella, Lutiella, Lyngbya, Lysinibacillus, Macrococcus, Magnetococcus, Magnetospirillum, Mahella, Mannheimia, Maricaulis, Marinithermus, Marinobacter, Marinomonas, Mariprofundus, Maritimibacter, Marvinbryantla, Megasphaera, Meiothermus, Melissococcus, Mesorhizobium, Methylacidiphilum, Methylibium, Methylobacillus, Methylobacter, Methylobacterium, Methylococcus, Methylocystis, Methylomlcroblum, Methylophaga, Methylophleales, Methylosinus, Methyloversatilis, Methylovorus, Microbacterium, Micrococcus, Microcoleus, Microcystis, Microlunatus, Micromonospora, Mitsuokella, Mobluncus, Moorella, Moraxella, Moritella, Mycobacterium, Myxococcus, Nakamurella, Natranaerobius, Neisserla, Neorickettsia, Neptuniibacter, Nitratifractor, Nitratiruptor, Nitrobacter, Nitrococcus, Nitrosomonas, Nitrosospira, Nitrospira, Nocardia, Nocardioides, Nocardiopsis, Nodularia, Nostoc, Novosphingobium, Oceanibulbus, Oceanicaulis, Oceanicola, Oceanithermus, Oceanobacillus, Ochrobactrum, Octadecabacter, Odyssella, Oligotropha, Olsenella, Opitutus, Oribacterium, Orientia, Omithinibacillus, Oscilatoria, Oscillochloris, Oxalobacter, Paenibacillus, Pantoea, Paracoccus, Parascardovia, Parasutterella, Parvibaculum, Parvimonas, Parvularcula, Pasteurella, Pasteuria, Pectobacterium, Pediococcus, Pedosphaera, Pelagibaca, Pelagibacter, Pelobacter, Pelotomaculum, Peptoniphius, Peptostreptococcus, Persephonella, Petrotoga, Phaeobacter, Phascolarctobacterium, Phenylobacterium, Photobacterlum, Pirellula, Planctomyces, Planococcus, Plesiocystis, Polaromonas, Polaromonas, Polymorphum, Polynucleobacter, Poribacteria, Prochlorococcus, Propionibacterium., Proteus, Providencia, Pseudoalteromonas, Pseudoflavonifractor, Pseudomonas, Pseudonocardia, Pseudoramibacter, Pseudovibrio, Pseudoxanthomonas, Psychrobacter, Psychromonas, Puniceispkillum, Pusilllmonas, Pyramidobacter, Rahnella, Ralstonia, Raphidiopsis, Regiella, Reinekea, Renibacterium, Rhizobium, Rhodobacter, Rhodococcus, Rhodoferax, Rhodomicrobium, Rhodopirellula, Rhodopseudomonas, Rhodospirillum, Rickett-sia, Rickettsiella, Riesia, Roseburia, Roseibium, Roseiflexus, Roseobacter, Roseomonas, Roseovarius, Rothia, Rubrivivax, Rubrobacter, Ruegeria, Ruminococcus, Ruthia, Saccharomonospora, Saccharophagus, Saccharopolyspora, Sagittula, Salinispora, Salmonella, Sanguibacte, Scardovia, Sebaldella, Segniliparus, Selenomonas, Serratia, Shewanella, Shigella, Shuttleworthia, Sideroxydans, Silicibacter, Simonslella, Sinorhizoblum, Slackia, Sodalls, Solibacter, Solobacterium, Sorangium, Sphaerobacter, Sphingobium, Sphingomonas, Sphingopyxis, Spirochaeta, Sporosarcina, Stackebrandtla, Staphylococcus, Starkeya, Stenotrophomonas, Stigmatella, StreptobacWllus, Streptococcus, Streptomyces, Streptosporangium, Subdoligranulum, subvibrioldes, Succinatimonas, Sulfitobacter, Sulfobacillus, Sulfuricurvum, Sulfurhydrogenibium, Sulfurimonas, Sulfurospirillum, Sulfurovum, Sutterella, Symbiobacterum, Synechocystis, Syntrophobacter, Syntrophobotulus, Syntrophomonas, Syntrophothermus, Syntrophus, talwanensis, Taylorella, Teredinibacter, Terriglobus, Thalassiobium, Thauera, Thermaerobacter, Thermanaerovibrlo, Thermincola, Thermoaneerobacter, Thermoanaerobacterum, Thermobaculum, Thermobifida, Thermobispora, Thermocrinis, Thermodesulphateator, Thermodesulfobacterlum, Thermodesulfoblum, Thermodesulfovibrlo, Thermomicrobium, Thermomonospora, Thermosediminibacter, Thermosinus, Thermosipho, Thermosynechococcus, Thermotoga, Thermovibrio, Thermus, Thloalkallmicrobium, Thioalkalivibrio, Thiobacillus, Thiomicrospira, Thiomonas, Tolumones, Treponema, tribocorum, Trichodesmium, Tropheryma, Truepera, Tsukamurella, Turicibacter, Variovorax, Veillonella, Verminephrobacter, Verrucomicroblum, Verrucosispora, Vesicomyosocius, Vibro, Vibrionales, Victivallis, Weissella, Wigglesworthia, Wolbachia, Wolinella, Xanthobacter, Xanthomonas, Xenorhabdus, Xylanimonas, Xylella, Yersinia, Zinderia and Zymomonas.

In particular, the recombinant cell may be selected from the group consisting of *Bacillus subtilis, Burkholderia thailandensis, Corynebacterium glutamicum,* Cyanobacteria, *E. coli, Klebsiella oxytoca, Pseudomonas fluorescens, Pseudomonas putida, Pseudomonas stutzeri,* and *Rhizobium meliloti,* More in particular, the microbial cell may be *E. coli.* These bacterial cells do not naturally produce glycerol dehydratase and are genetically modified to increase the expression relative to the wild type cell of glycerol dehydratase.

In another example, the recombinant cell may be selected from the group consisting of *Citrobacter freundii, C. butyricum, C. acetobutylicum, E. agglomerans, L. reuteri,* and *K. pneumoniae.* These bacterial cells naturally produce glycerol dehydratase and are further genetically modified to increase the expression relative to the wild type cell of glycerol dehydratase. Seyfried M, et al. (1996) J. Bacteriol. 178, 5793-5796; Ulmer C, at al. (2007) Chem Biochem Eng Quart 21(4): 321-326, and van Pijkeren J-P, at al. (2012) Bioengineered 3:209-217 describe ways in which this bacterial cells which naturally produce glycerol dehydratase may be further genetically modified to increase the expression relative to the wild type cell of glycerol dehydratase.

The bacterial cells used for production of 3-HPA may be used as free or immobilized cells. In particular, the aqueous medium used according to any aspect of the present invention may be capable of maintaining the growth of these cells without being toxic to the cell. More in particular, the aqueous medium according to any aspect of the present invention may be capable of maintaining the production of 3-HPA without being toxic to the cell.

The method according to any aspect of the present invention comprises a step (b) separating the 3-HPA bound chitosan and/or chitosan comprising polymers. This step occurs after the 3-HPA in the aqueous medium has been brought into contact with chitosan and/or chitosan comprising polymers to form 3-HPA bound chitosan and/or chitosan comprising polymers. The binding time may vary depending on the mW and/or grade of chitosan and/or chitosan comprising polymers used and/or the concentration of 3-HPA and chitosan in the medium. The term 'binding time' as used herein, refers to the amount of time needed for 3-HPA to bind to the available chitosan and/or chitosan comprising polymers during step (a) the contacting. The binding time starts when the aqueous medium comprising 3-HPA is brought into contact with the chitosan and/or chitosan comprising polymers. The binding period ends when step (b) starts where the 3-HPA bound chitosan and/or chitosan comprising polymers are separated. In particular, the binding time may be at least 5 minutes. The binding time may be 5-60 minutes. More in particular, the binding time may be at least 10, 15, 20, 25, 30, 35, 40, 45, 50 or 55 minutes. Even more in particular, the binding time may be 30 minutes. A skilled person would easily be able to determine the suitable binding time depending on the amount of 3-HPA in the aqueous medium and the amount of chitosan and/or chitosan comprising polymers used. A longer binding time may be needed when chitosan and/or chitosan comprising polymers are found to be the limiting factor and more are added to the reaction.

In one example, the method according to any aspect of the present invention may be carried out in an aqueous medium with a pH between 5 and 8, 5.5 and 7 or the like. The pressure may be between 1 and 10 bar. The temperature may be any temperature between 20-70° C. In particular, the temperature may be selected from the group consisting of about 25, 30, 35, 40, 45, 50, 55, 60, 65, and 70. In one example, the temperature may be room temperature, about 22° C.

As used herein, the terms "about" and "approximately", as applied to one or more particular cell culture conditions refer to a range of values that are similar to the stated reference value for that culture condition or conditions. In certain examples, the term "about" refers to a range of values that fall within 25, 20, 19, 18, 17, 16, 15, 14, 13, 12, 11, 10, 9, 8, 7, 6, 5, 4, 3, 2, 1 percent or less of the stated reference value for that culture condition or conditions. For example, an amount of an ingredient employed in a mixture when modified by "about" includes the variation and degree of care typically employed in measuring in an experimental condition in production plant or lab.

The amount of chitosan and/or chitosan comprising polymers added in step (a) may be dependent on several factors including the concentration of 3-HPA in the aqueous medium, 3-HPA volume, molecular weight of chitosan, degree of acetylation of chitosan and contact/binding time between the chitosan and 3-HPA in the aqueous medium. A skilled person may be capable of determining the concentration of chitosan and/or chitosan comprising polymers that needs to be added to the 3-HPA in the aqueous medium. For example, the ratio of chitosan and/or chitosan comprising polymers to 3-HPA may be based on the binding capacity of the chitosan and/or chitosan comprising polymers. 1 g of chitosan and/or chitosan comprising polymers may be capable of binding 25 mg to 2000 mg of 3-HPA. In particular, 1 g of chitosan and/or chitosan comprising polymers may be capable of binding about 25, 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1025, 1050, 1075, 1100, 1125, 1150, 1175, 1200, 1225, 1250, 1275, 1300, 1325, 1350, 1375, 1400, 1425, 1450, 1475, 1500, 1525, 1550, 1575, 1600, 1625, 1650, 1675, 1700, 1725, 1750, 1775, 1800, 1825, 1850, 1875, 1900, 1925, 1950, 1975, 2000 mg of 3-HPA. More in particular, 1 g of chitosan and/or chitosan comprising polymers may be capable of binding 50-2000, 50-1000, 50-500, 100-2000, 100-1500, 100-500 mg of 3-HPA. A skilled person would be capable of varying the concentration of chitosan and/or chitosan comprising polymers in the aqueous solution to obtain the most efficient binding.

In step (b), separation of the 3-HPA bound chitosan and/or chitosan comprising polymers may be carried out. Any separating means known in the art may be used in this step. A skilled person would be capable of identifying the suitable means of separating 3-HPA bound chitosan and/or chitosan comprising polymers by simple trial and error. In particular, the step of separating is selected from the group consisting of filtration, centrifugation, decantation and combinations thereof. This step of separation may result in separating the aqueous solution from the 3-HPA bound chitosan and/or chitosan comprising polymers. In one example where 3-HPA may be formed biotechnologically using microbial cells, step (b) according to any aspect of the present invention may lead to the separation of (1) aqueous medium comprising the cells and unreacted carbon source and (2) 3-HPA bound chitosan and/or chitosan comprising polymers. Since 3-HPA in the aqueous medium may be considered toxic to the cell, the removal of 3-HPA from the aqueous medium allows the cells to survive and continue to produce 3-HPA from the remaining unreacted carbon source.

The combination of steps (a) and (b) according to any aspect of the present invention, allows for most of the 3-HPA to be removed from the aqueous medium as the 3-HPA is bound to the chitosan and/or chitosan comprising polymers. In particular, at least about 50, 60, 70, 80, 90, 95, 98, or 99% of all the 3-HPA found in the aqueous medium may be bound to the added chitosan and/or chitosan comprising polymers and removed from the aqueous medium by the separation step (b). A skilled person would understand that the binding of 3-HPA to chitosan and/or chitosan comprising polymers may be dependent on the concentrations of 3-HPA and chitosan and/or chitosan comprising polymers.

The method according to any aspect of the present invention comprises a further step (c) of washing the 3-HPA bound chitosan and/or chitosan comprising polymers with at least one washing medium. The washing medium also known as the elution solution/medium may be selected from the group consisting of water, ethanol, ammonium sulfate solution, ammonium carbonate solution, acetic acid, formic acid, citric acid, carbonic acid, trifluoroacetic acid, hydrochloric acid, sulphuric acid, phosphoric acid and mixtures thereof. In one example when the washing medium may be ethanol, the ethanol may be 25%, 50% 75% or 99.5% ethanol. In another example, the washing medium may be a mixture of distilled water, 50% ethanol, 6% ammonium carbonate and 0.1 M HCl mixture. In one example, the washing medium comprises 0.1 M pH 7.5 Tris buffer. In another example, the washing medium comprises 0.5 M pH 7.5 Tris buffer or combined (2 tetrahydorfuran "THF": 1 acetone:0.03 HCl). In particular, the washing medium is selected from the group water, acid and mixtures thereof. More in particular, the adds may be selected from the group consisting of acetic acid, formic acid, citric add, carbonic acid, trifluoroacetic acid, hydrochloric acid, sulphuric acid, phosphoric acid and mixtures thereof. Even more in particular, the acid may be selected from the group consisting of acetic acid, formic acid, citric acid, carbonic acid and mixtures thereof. A skilled person may use any one of these options as a first washing medium in step (c) of the method according to any aspect of the present invention. The concentration of acid used in step (c) may be about 1 M.

In one example, when acid is used as a washing medium in step (c) according to any aspect of the present invention, the ratio of acid to 3-HPA used may be selected from the range of 0.2 to 4. In another example, the ratio may be selected from the range of 0.2 to 3, 0.5 to 4, 0.5 to 3, 0.2 to 4, 0.2 to 2 and the like. A skilled person may be capable of identifying the best ratio to option the highest yield of 3-HPA extract in the least diluted form.

The method according to any aspect of the present invention may comprise at least one washing step. After washing, step (b) may be repeated to separate the 3-HPA from chitosan and/or chitosan comprising polymers. In one example, centrifugation may be used as a method of separation. The supernatant obtained from this separation step may comprise 3-HPA.

In another example, the washing step (c) may be carried out at least twice according to any aspect of the present invention. In this example, when the washing step is carried out twice, two different washing mediums may be used. In one example, water may be used as a first washing medium and an acid may be used as a second washing medium. The statement 'the two different washing mediums are (i) water and (ii) at least one acid or mixtures thereof' do not limit the order of use of the two different washing mediums. This statement only states that two different mediums are used consecutively but they may be used in any order. The use of numeral (i) and (ii) do not limit the order of use of the two washing mediums. Therefore, in one example, (i) water may be used as the first washing medium and then (ii) at least one acid or mixtures thereof may be used as the second washing medium. In another example, (ii) at least one acid or mixtures thereof may be used as the first washing medium and then (i) water may be used as the second washing medium. The only essential feature in step (c) may be that when the washing step is repeated, two different washing mediums may be used.

In one example, (c) the washing step is carried out at least twice consecutively in two different washing mediums of (i) water and (ii) citric acid in any order.

At the end of step (c), almost al the 3-HPA bound to the chitosan and/or chitosan comprising polymers may have released to result in free 3-HPA and free chitosan and/or chitosan comprising polymers. The chitosan and/or chitosan comprising polymers may then be recycled by returning them to step (a). The method according to any aspect of the present invention provides a cost effective means of separating 3-HPA from an aqueous medium. This method may be considered cost-effective as there may be no waste of chitosan and/or chitosan comprising polymers as they can be indefinitely reused. Further, chitosan and/or chitosan comprising polymers have a special property of being capable of adsorption and desorption of 3-HPA. Whether or not chitosan and/or chitosan comprising polymers choose to adsorb or desorb 3-HPA depends in particular to the surrounding 3-HPA concentration which may affect the pH and/or temperature. For example, the chitosan and/or chitosan comprising polymers adsorb 3-HPA from the aqueous medium when the surrounding 3-HPA concentration is high. When the 3-HPA concentration of the surrounding solution, such as in the washing medium in step (c) is low, chitosan and/or chitosan comprising polymers desorb 3-HPA to the surrounding washing medium. Accordingly, the binding affinity of the chitosan and/or chitosan comprising polymers vary depending on the surrounding 3-HPA concentration. A skilled person would easily be able to identify the concentration of 3-HPA needed in the aqueous solution to switch on or switch off the adsorption or desorption capability of chitosan and/or chitosan comprising polymers.

The concentration of 3-HPA in an aqueous medium may be measured using any method known in the art. In one example, acrolein test may be used for quantitative analysis of 3-HPA. Acrolein test is described at least in Vollenweider, S., et al., Journal of agricultural and food chemistry, 2003. 51(11): p. 3287-3293 and Circle, S. Ind Eng Chem Anal Ed, 1945. 17: p. 259-262. In summary, a suitably diluted sample with 3-HPA may be mixed with HCl at a ratio of 3:1 for the dehydration of 3-HPA to acrolein. DL-tryptophan may then be added to obtain an acrolein-chromophore complex (purple) which may be quantified by absorbance at 560 nm on a spectrophotometer using acrolein as standard.

In one example, 3-HPA may be produced by at least one microorganism from at least one carbon source. In particular, the carbon source may be glycerol or sugars like glucose. The microorganism may be naturally capable of dehydrating glycerol to 3-HPA. In another example, the microorganism may be genetically modified to be able to convert glycerol to 3-HPA. In particular, the genetically modified cell may be genetically modified to increase the expression relative to the wild type cell of at least one enzyme selected from the group consisting of diol dehydratase and/or glycerol dehydratase, and optionally diol dehydratase reactivating factor and/or glycerol dehydratase reactivating factor.

The genetically modified cell or microorganism may be genetically different from the wild type cell or microorganism. The genetic difference between the genetically modified microorganism according to any aspect of the present invention and the wild type microorganism may be in the presence of a complete gene, amino acid, nucleotide etc. in the genetically modified microorganism that may be absent in the wild type microorganism. In one example, the genetically modified microorganism according to any aspect of the present invention may comprise enzymes that enable the microorganism to dehydrate glycerol to 3-HPA. The wild type microorganism relative to the genetically modified microorganism according to any aspect of the present invention may have none or no detectable activity of the enzymes that enable the genetically modified microorganism to dehydrate glycerol to produce 3-HPA. As used herein, the term 'genetically modified microorganism' may be used interchangeably with the term 'genetically modified cell'. The genetic modification according to any aspect of the present invention may be carried out on the cell of the microorganism.

The phrase "wild type" as used herein in conjunction with a cell or microorganism may denote a cell with a genome make-up that is in a form as seen naturally in the wild. The term may be applicable for both the whole cell and for individual genes. The term "wild type" therefore does not include such cells or such genes where the gene sequences have been altered at least partially by man using recombinant methods.

The phrase "increased activity of an enzyme", as used herein is to be understood as increased intracellular activity. Basically, an increase in enzymatic activity can be achieved by increasing the copy number of the gene sequence or gene sequences that code for the enzyme, using a strong promoter or employing a gene or allele that codes for a corresponding enzyme with increased activity and optionally by combining these measures. Genetically modified cells used in the method according to the invention are for example produced by transformation, transduction, conjugation or a combination of these methods with a vector that contains the desired gene, an allele of this gene or parts thereof and a vector that makes expression of the gene possible. Heterologous expression is in particular achieved by integration of the gene or of the alleles in the chromosome of the cell or an extrachromosomally replicating vector. Similarly, a decreased activity of an enzyme refers to decreased intracellular activity. In one example, the increased expression of an enzyme according to any aspect of the present invention may be 5, 10, 15, 20, 25, 30, 25, 40, 45, 50, 55, 60, 65, 70, 75, 80, 85, 90, 95 or 100% more relative to the expression of the enzyme in the wild type cell. In some examples, the increase in expression of the enzyme may be even more than 100%. Similarly, the decreased expression of an enzyme according to any aspect of the present invention may be 5, 10, 15, 20, 25, 30, 25, 40, 45, 50, 55, 60, 65, 70, 75, 80, 85, 90, 95 or 100% less relative to the expression of the enzyme in the wild type cell.

In one example, the 3-HPA is formed from glycerol in a first vessel using at least one microbial cell. A skilled person would be capable of varying the conditions in the vessel to maintain efficient and/or continuous production of 3-HPA. In order to extract 3-HPA in a non-toxic manner, the method according to any aspect of the present invention may be practiced. The use of chitosan and/or polymers comprising chitosan do not reduce the enzyme activity of the cell, thus allowing the cells to continue to produce 3-HPA, allowing for the production of 3-HPA to be maintained and for the cells to be reused. In this example, the cells may be physically separated from the chitosan and/or polymers comprising chitosan using any method known in the art. In one example, the cells may be immobilized in a gel, matrix or membrane so that the chitosan may not bind the cells. The 3-HPA produced by the cells may be released into the aqueous medium where the chitosan is freely present. This way, there may be no contact between the chitosan and/or polymers comprising chitosan and the cells. The chitosan thus does not inhibit the cells from producing 3-HPA. 3-HPA may be continuously produced as the chitosan and/or polymers comprising chitosan bind the 3-HPA for the extraction process in step (a) of the method according to any aspect of the present invention. The glycerol may be added in a fed-batch or continuous mode.

In another example, at least two vessels may be used according to any aspect of the present invention. In one vessel, glycerol may be brought into contact with the microbial cells for production of 3-HPA in the aqueous medium. The microbial cells may be freely present in the first vessel. The medium with the 3-HPA may then be transferred into a second vessel (without the cells). The second vessel may comprise chitosan and/or polymers comprising chitosan. The 3-HPA may bind to the chitosan and/or polymers comprising chitosan in the second vessel. The medium with substantially absent 3-HPA may then be recycled into the first vessel. This flow between the two vessels may be continuous and maintained.

According to another aspect of the present invention, there is provided a method of using the 3-HPA extracted from the method according to any aspect of the present invention to produce 1,3-propanediol, 3-hydroxypropionic acid, acrolein, acrylic acid and an acrylic ester.

EXAMPLES

Figure 1:
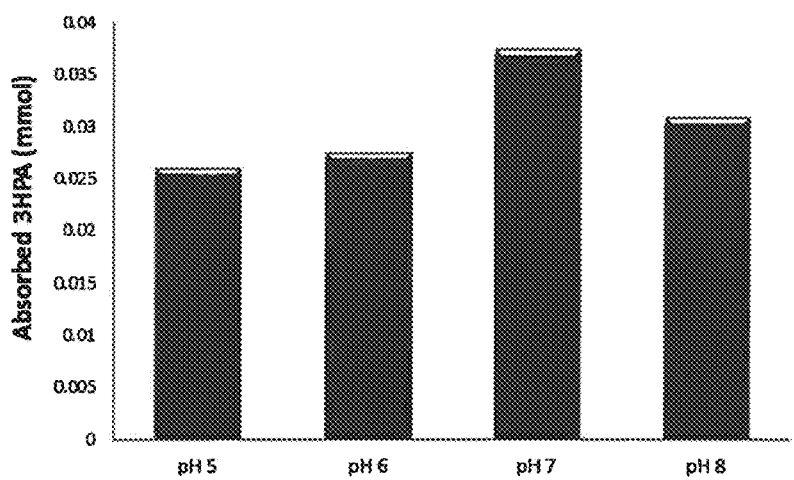
FIG. 1 is a graph showing the adsorption of 3-HPA (at different pH using buffers) to medium molecular weight chitosan (0.01 g).

The foregoing describes preferred embodiments, which, as will be understood by those skilled in the art, may be subject to variations or modifications in design, construction or operation without departing from the scope of the claims. These variations, for instance, are intended to be covered by the scope of the claims.

Example 1

Low and Medium Molecular Weight Chitosan Evaluated as Scavengers for 3-HPA

Initially 0.1 g chitosan powder (low molecular weight component has a viscosity of 20-300 cP (1 wt. % in 1% acetic acid—75 to 85% deacetylation) and the medium molecular weight component has viscosity of 200-800 cP (1 wt. % in 1% acetic acid—75 to 85% deacetylation) as supplied commercially by Sigma) was added to 5 ml of 3-HPA solution (95.6 mM), pH 7. 3-Hydroxypropionaldehyde (3-HPA) was produced using *Lactobacillus reuteri* as described in Sardari et al. 2013 (Sardari, R. R., et al., Biotechnology and Bioengineering, 2013. 110(4): p. 1243-1248). The mixture was mixed for 30 min at room temperature, 22° C., after which the chitosan was separated by centrifugation at 3000×g for 5 min. The concentration of residual 3-HPA in the supernatant 1 was measured by acrolein test. There was 60.1 mM of 3-HPA when low Mw chitosan was used and 53.1 mM of 3-HPA when medium Mw chitosan was used. The chitosan was then washed once by resuspension in 10 ml distilled water at room temperature for 10 min followed by centrifugation and determination of the 3-HPA concentration in the supernatant 2 using the acrolein test. Finally, 10 ml of 1 M organic acid (Acetic acid (Sigma Aldrich), Formic acid (Sigma Aldrich), Citric acid (Merck), Carbonic acid) was each separately added to the chitosan, mixed for 15 min, then centrifuged and the concentration of 3-HPA in the supernatant 3 was determined using the acrolein test.

Acrolein test was used for quantitative analysis of 3-HPA. Two hundred microliter of a suitably diluted sample was mixed with 600 µl HCl for the dehydration of 3-HPA to acrolein. DL-tryptophan (150 µl) was added to the mixture, thereby obtaining an acrolein-chromophore complex (purple) which was quantified by absorbance at 560 nm on a spectrophotometer using acrolein as standard (Vollenweider, S., et al., Journal of Agricultural and Food Chemistry, 2003. 51(11): p. 3287-3293; Circle, S. Ind Eng Chem Anal Ed, 1945. 17: p. 259-262.).

The results are shown in Table I below. Almost 50% of the bound 3-HPA was recovered in the water fraction (Elution 1) and the residual 50% was recovered in the organic acid fraction (Elution 2). The recovery (elution) of bound 3-HPA was quantitative.

TABLE 1

Binding and elution of 3-HPA to/from low and medium molecular weight chitosan powder

| | Chitosan Mwt | | | | | | | |
|---|---|---|---|---|---|---|---|---|
| | Low | Med | Low | Med | Low | Med | Low | Med |
| | Elution System | | | | | | | |
| | Acetic acid | | Formic acid | | Citric acid | | Carbonic acid | |
| Loading (mmol) | 0.183 | 0.213 | 0.183 | 0.213 | 0.183 | 0.213 | 0.183 | 0.213 |
| E1 (mmol) | 0.093 | 0.111 | 0.091 | 0.113 | 0.095 | 0.110 | 0.098 | 0.122 |
| E2 (mmol) | 0.092 | 0.109 | 0.097 | 0.108 | 0.100 | 0.111 | 0.091 | 0.099 |
| Total elution | 0.185 | 0.220 | 0.188 | 0.220 | 0.195 | 0.220 | 0.189 | 0.221 |
| % eluted | 101.0% | 103.4% | 102.6% | 103.4% | 106.4% | 103.4% | 103.1% | 103.8% |

Example 2

Effect of pH on Binding Capacity

The effect of the solution pH on the binding capacity was also investigated using medium molecular weight chitosan as scavenger. Binding capacity was measured using the same method used in Example 1. The results are shown in FIG. 1. pH 7 was found optimum for 3-HPA binding.

Example 3

Effect of Chitosan Molecular Weight and Concentration on 3-HPA Binding

Different concentrations (2%, 4% and 6%, respectively) of low- and medium-molecular weight chitosan were dissolved overnight in 2%, 4% or 6% of acetic acid, respectively. Low molecular weight component has a viscosity of 20-300 cP (1 wt. % in 1% acetic acid—75 to 85% deacetylation) and the medium molecular weight component has viscosity of 200-800 cP (1 wt. % in 1% acetic acid—75 to 85% deacetylation) as supplied commercially by Sigma. The resulting viscous solutions were dropped in 2%, 4% and 6% of sodium hydroxide solution, respectively through a thick needle. The resulting beads were washed thoroughly with Milli-Q quality water and then with phosphate buffer (pH 7, 50 mM). One g of swollen beads was then placed in a 15-ml falcon tube and 3-HPA solution (5 ml of 46.6 mM, pH 7) was added to the beads and the tubes were mixed on a rocking table for 12 h. The concentration of residual 3-HPA in the solution was measured by acrolein test (as described under example 1) and the binding capacity was calculated for each chitosan molecular weight and concentration.

Figure 2:
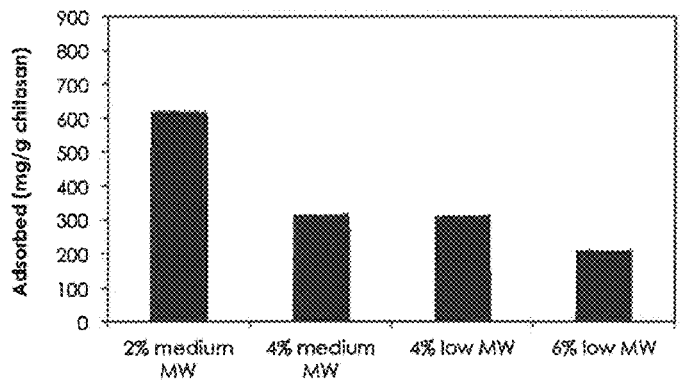
FIG. 2 is a graph showing the effect of molecular weight and concentration of chitosan used for making beads on the binding capacity for 3-HPA.

From the data as shown in FIG. 2 it is clear that there was no difference between the two molecular weights of chitosan for the binding capacity of 3-HPA when used at the same concentration (4%). However, by decreasing the concentration of the chitosan, the binding capacity was increased. In case of low molecular weight chitosan, the beads were extremely fragile at a concentration of 2% and did not solidify when dropped in sodium hydroxide solution. On the other hand, it gave highly stable beads when used at concentrations of 4% and 6%. The opposite was true for medium molecular weight chitosan where at a concentration of 2% and 4%, the beads was highly stable, however, for the 6% chitosan the solution was highly viscous. Hence, 2% medium molecular weight chitosan was found optimum for use in 3-HPA capture due to easy formulation and high binding capacity reaching 766 mg/g chitosan.

Example 4

Effect of Duration of 3-HPA Binding to Chitosan on Elution

To four 50 ml falcon tubes, each containing 1 g wet beads prepared from medium molecular weight chitosan (2%) in 2% acetic acid, 5 ml of 14 mM 3-HPA solution, pH 7 was added and shaken at room temperature for different time intervals (0.5, 1, 1.5 and 2 h, respectively). At each time period, one tube was removed, the solution separated and beads washed once with 5 ml MQ water and the amount of 3-HPA bound to the resin was calculated. Subsequently 3-HPA was eluted using 2.5 ml of elution system (ethanol/ammonium sulfate/HCl, 50%/6%/0.1 M) and the amount of 3-HPA in the eluent was measured.

Figure 3:
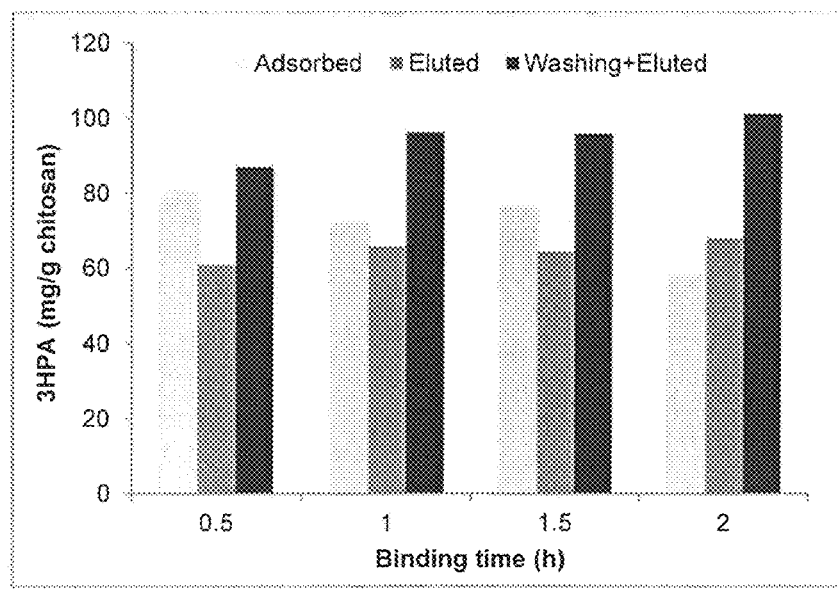
FIG. 3 is a graph showing the effect of adsorption time on elution of 3-HPA from wet chitosan beads (3% medium molecular weight chitosan.

As can be seen in FIG. 3, the amount of 3-HPA bound during 0.5-2 h varied between 60 and 80 mg/g chitosan. The amount of 3-HPA eluted from the beads was on average 91.7±17%. Significant amount of 3-HPA was also recovered in the washing step that could be the aldehyde that was physically adsorbed to the beads.

Example 5

Adsorption/Desorption of 3-HPA Using Cross-Linked Chitosan Beads: Using High Initial 3-HPA Concentration and Different Elution Systems In three 50 ml falcon tubes, 0.05 g cross-linked chitosan beads were mixed with 5 ml of 113 mM 3-HPA solution, pH 7 for 30 min on a rocking table.

X-linked chitosan beads were prepared based on the method used by Wan Ngah et al. (2008). First, 1 g of medium molecular weight chitosan was dissolved in 35 ml of 5% (v/v) acetic acid. The mixture was shaken slowly overnight on a rocking table. The dissolved chitosan solution was filled in a 100 ml syringe and dropped through a needle into 250 ml sodium hydroxide solution (2% w/v). The formed wet beads were then washed by distilled water to remove any NaOH and air-dried (dry beads). For X-linking the chitosan beads, 0.1 M epichlorohydrin (ECH) solution was prepared and the pH was adjusted to 10 using 0.067 M NaOH. The dry chitosan beads were suspended in 62.5 ml of the 0.1 M ECH solution to obtain a ratio of 1:1 with chitosan (mol CH2O: mol CH2OH). The beads suspension was stirred continuously on a magnetic stirrer at 200 rpm for 2 h. Then the X-linked beads were washed with hot-followed by cold distilled water to remove any excess ECH solution, and then air-dried.

Figure 4A:
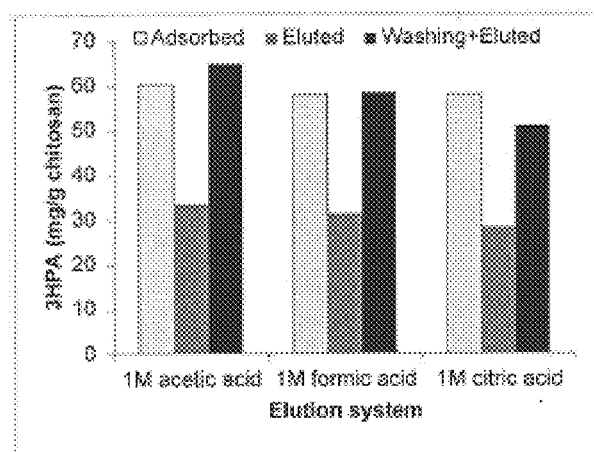
FIG. 4A is a graph showing the adsorption, washing and elution of high concentration of 3-HPA (113 mM) from cross-linked beads using different elution system where the concentration of the elution medium is 1 M.
Figure 4B:
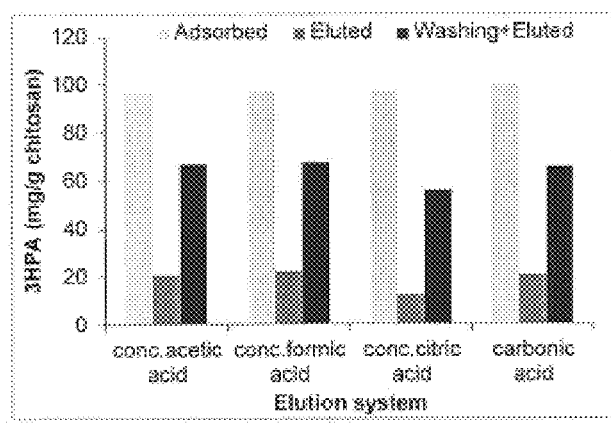
FIG. 4B is a graph showing the adsorption, washing and elution of high concentration of 3-HPA (113 mM) from cross-linked beads using different elution system where concentrated elution mediums are used.

The binding to the x-linked chitosan beads was followed by a washing step using 10 ml of distilled water and elution by 5 ml of 1 M acetic acid, 1 M formic acid, and 1 M citric acid, respectively, for 30 min (FIG. 4 A). A parallel experiment was performed in 4 falcon tubes using 0.1 g cross-linked chitosan and different concentrated acids (acetic acid, formic acid, citric acid, and carbonic acid) for elution (FIG. 4 B).

As seen from FIG. 4, low concentration of acids, could release higher amount of 3-HPA, and 1 M acetic acid has the highest recovery.

Example 6

Figure 5:
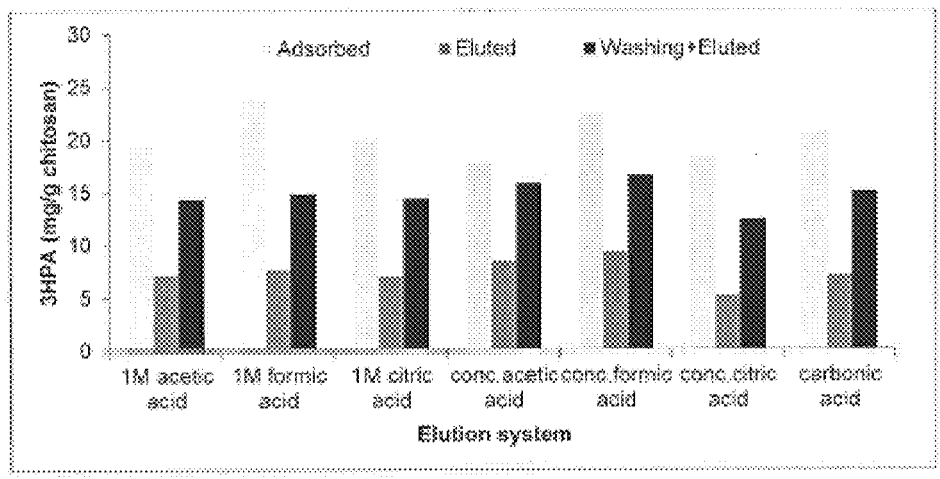
FIG. 5 is a graph showing the adsorption, washing and elution of low concentration of 3-HPA (18 mM) from cross-linked beads using different elution systems. From the left to the right: 1 M acetic acid; 1 M formic acid; 1 M citric acid; conc. acetic acid; conc. formic acid; conc. citric acid and carbonic acid.

Adsorption/Desorption of 3-HPA Using Cross-Linked Chitosan Beads: Using Low Initial 3-HPA Concentration and Different Elution Systems In seven 50 ml falcon tubes, 0.05 g of cross-linked beads were mixed with 5 ml of 18 mM 3-HPA solution, pH 7 for 30 min on a rocking table. The binding was followed by a washing step using 10 ml of distilled water and elution by 5 ml of different acids with different concentration as elution system for 30 min. The results are shown in FIG. 5.

The recovery of 3-HPA was 89, 74, 67, and 73% using concentrated acetic acid, concentrated formic acid, and concentrated citric acid, respectively. Also, the recovery of 3-HPA was 74, 62, 72, and 73 using 1 M acetic acid, 1 M formic acid, 1 M citric acid, and carbonic acid.

It can be concluded that adsorption and recovery are better at high initial 3-HPA concentration and 3-HPA is not stable in high concentration of acid.

The invention claimed is:

1. A method of extracting 3-hydroxypropionaldehyde (3-HPA) and/or derivatives thereof from an aqueous solution comprising 3-HPA, the method comprising:
   (a) contacting the aqueous solution with chitosan and/or chitosan comprising polymers;
   (b) separating the 3-HPA bound chitosan and/or chitosan comprising polymers; and
   (c) washing the 3-HPA bound chitosan and/or chitosan comprising polymers at least once with a washing medium;
   wherein 3-HPA and/or derivatives thereof is in the washing medium.

2. The method according to claim 1, wherein the washing medium is selected from the group consisting of water, an acid and mixtures thereof.

3. The method according to claim 2, wherein the acid is selected from the group consisting of acetic acid, formic acid, citric acid, carbonic acid, trifluoroacetic acid, hydrochloric acid, sulphuric acid, phosphoric acid and mixtures thereof.

4. The method according to claim 1, wherein (c) the washing step is carried out at least twice consecutively in at least two different washing mediums.

5. The method according to claim 4, wherein the two different washing mediums are (i) water and (ii) at least one acid or mixtures thereof.

6. The method according to claim 1, wherein chitosan and/or chitosan comprising polymers are recyclable.

7. The method according to claim 1, wherein the aqueous solution comprises 1 g of chitosan and/or chitosan comprising polymers for binding 50-2000 mg of 3-HPA.

8. The method according to claim 1, wherein (b) the step of separating is selected from the group consisting of filtration, centrifugation, decantation and combination thereof.

9. The method according to claim 1, wherein the chitosan and/or chitosan comprising polymers are capable of adsorption and desorption of 3-HPA.

10. The method according to claim 1, wherein the 3-HPA in aqueous solution is produced from at least one carbon source by at least one microorganism.

11. The method according to claim 10, wherein the microorganism is selected from the group consisting of *Lactobacillus reuteri, Klebsiella pneumoniae, Citrobacter freundii, Clostridium butyricum, Clostridium acetobutylicum,* and *Enterobacter agglomerans*.

12. The method according to claim 10, wherein the microorganism is a recombinant microorganism expressing glycerol dehydratase.

13. The method according to claim 10, wherein the carbon source is selected from the group consisting of glycerol and glucose.

14. The method according to claim 10, wherein the microorganisms are removed prior to (a) of contacting the aqueous solution with chitosan and/or chitosan comprising polymers.

15. The method according to claim 1, wherein (c) the washing step is carried out at least twice consecutively in two different washing mediums of (i) water and (ii) citric acid.

* * * * *